(12) United States Patent
He et al.

(10) Patent No.: US 7,449,442 B2
(45) Date of Patent: Nov. 11, 2008

(54) EGFR INHIBITORS PROMOTE AXON REGENERATION

(75) Inventors: Zhigang He, Boston, MA (US); Vuk Koprivica, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 276 days.

(21) Appl. No.: 11/180,070

(22) Filed: Jul. 12, 2005

(65) Prior Publication Data

US 2007/0014792 A1    Jan. 18, 2007

(51) Int. Cl.
*A61K 31/00* (2006.01)

(52) U.S. Cl. .................... 514/1; 424/143.1

(58) Field of Classification Search .............. None
See application file for complete search history.

(56) References Cited

OTHER PUBLICATIONS

Purves, Dale, et al (Eds.), Neuroscience, 2001, Sinauer Associates, Inc., 2nd Edition, pp. 75, 367, 400, 403, 554, 555 and 678.*
Vickers. A vaccine against Alzheimers's disease: developments to date. Drugs Aging 2002; 19(7):487-94.*
Stokes et al. Experimental modeling of human spinal cord injury: a model that crosses the species barrier and mimic the spectrum of human cytopathology, Spinal Cord 40: 101-109, 2002.*
Talac et al. Animal models of spinal cord injury for evaluation of tissue engineering treatment strategies, Biomaterials 25: 1505-1510, 2004.*
Mills et al. Strain and model differences in behavioral outcomes after spinal cord injury in rat,J. Neurotrauma Aug.;18(8):743-56, 2001.*
Mautes et al. Vascular events after spinal cord injury: contribution to secondary pathogenesis. Phys Ther. Jul. 2000;80(7):673-87.*
Koprivica et al. EGFR activation mediates inhibition of axon regeneration by myelin and chondroitin sulfate proteoglycans. Science. Oct. 7, 2005; 310(5745):106-10.*
Miller. Neuroscience. Cancer drugs may help injured nerve cells regrow their axons. Science. Oct. 7, 2005 ;310(5745):31.*

* cited by examiner

*Primary Examiner*—Elizabeth C. Kemmerer
*Assistant Examiner*—Gregory S Emch
(74) *Attorney, Agent, or Firm*—Nixon Peabody LLP

(57) ABSTRACT

Compositions and methods for promoting neural regeneration in a patient determined to have a lesion in a mature CNS neuron are disclosed. The method comprises the step of contacting the neuron with an EGFR inhibitor sufficient to promote regeneration of the neuron.

16 Claims, No Drawings

EGFR INHIBITORS PROMOTE AXON REGENERATION

This work was supported by Federal Grant Nos. R21NS041999 and DA015335. The U.S. government may have rights in any patent issuing on this application.

FIELD OF THE INVENTION

The field of the invention is the use of epidermal growth factor receptor (EGFR) inhibitors for promoting neural regeneration of lesioned mature CNS neurons.

BACKGROUND OF THE INVENTION

Failure of successful axon regeneration in the CNS is attributed not only to the intrinsic regenerative incompetence of mature neurons, but also to the environment encountered by injured axons. The inhibitory activity is principally associated with components of CNS myelin and chondroitin sulfate proteoglycans (CSPGs) in the glial scar at the lesion site (1-4). Recent studies suggested that three myelin proteins, myelin-associated glycoprotein (MAG), Nogo-A and oligodendrocyte myelin glycoprotein (OMgp), collectively account for the majority of the inhibitory activity in CNS myelin (4-6). The inhibitory activity of MAG, OMgp and the extracellular domain of Nogo-A may be mediated by a common receptor complex that consists of the ligand-binding Nogo-66 receptor (NgR) and its signaling co-receptors p75/TROY and Lingo-1 (7-13). However, little is known about how signaling events occurring at the axonal membrane are translated into specific cytoskeletal rearrangements underlying inhibition of axon regrowth. For instance, it is known that MAG and perhaps other myelin inhibitors are able to induce an elevation of intracellular $Ca^{2+}$ levels (14-16). But it is unclear how intracellular $Ca^{2+}$ signaling may be involved in the inhibition of axon regeneration.

The involvement of EGFR activation in development and differentiation of CNS neurons has been studied extensively. Goldshmit et al. (J Biol Chem (2004) 279:16349-16355) report that overexpression of SOCS2 in CNS neurons promotes neurite outgrowth, and that this outgrowth is blocked by addition of EGFR inhibitors PP3 and AG490. Wu et al. (Mol Biol Cell (2004) 15:2093-2104) report that the chondroitin sulfate proteoglycan versican V1 induces NGF-independent neuronal differentiation and promotes neurite outgrowth in cultured PC12 cells by enhancing EGFR and integrin activities, and that addition of the EGFR inhibitor AG1478 significantly blocks differentiation. Wildering et al. (J Neurosci (2001) 21:9345-9354) report that EGF promotes axonal regeneration of neurons of the crushed right internal parietal (RIP) nerve in the pond snail Lymnaea stagnalis and that inhibition of EGF action by the specific EGFR inhibitor PD153035 counteracts the effect of EGF on axonal regeneration. Li et al. (J Neurosci (2003) 23:6956-6964) report that PC12 cell lines with reduced EGFR signaling have reduced neurite outgrowth in response to NGF and that AG1478, a specific EGFR tyrosine kinase inhibitor, is cytotoxic to these cells.

In light of these reports our finding that suppressing EGFR function promotes significant regeneration of a lesioned adult CNS neuron in the presence of myelin inhibitory molecules was quite unexpected.

SUMMARY OF THE INVENTION

The invention provides compositions and methods for promoting neural regeneration of a lesioned CNS neuron. In one embodiment, the invention provides a method of promoting neural regeneration in a patient determined to have a lesion in a mature CNS neuron, the method comprising the step of contacting the neuron with an EGFR inhibitor sufficient to promote regeneration of the neuron.

In particular embodiments, the lesion is an axon lesion.

In particular embodiments, the lesion results from a traumatic injury, CNS degeneration, an optic nerve injury, or glaucoma.

In particular embodiments, the lesion results from a traumatic injury, and the contacting step is effected within 96, 48, or 24 hours of formation of the lesion.

In a particular embodiment, the lesion results from an acute spinal cord injury, and the method optionally comprises contacting the neuron with methylprednisolone sufficient to reduce inflammation of the spinal cord.

In a particular embodiment, the EGFR inhibitor is a small molecule selected from the group consisting of erlotinib, gefitinib, GW2016, GW572016, PKI166, CL-1033, EKB-569, and GW2016.

In another embodiment, the EGFR inhibitor is a monoclonal antibody selected from the group consisting of cetuximab, panitumumab, TheraCIM, EMD 72000, and MDX447.

In particular embodiments the EGFR inhibitor is administered to the patient orally or by injection.

In another embodiment, the EGFR inhibitor is contained within an implantable device.

In a particular embodiment, the method further comprises the step of detecting a resultant neural regeneration, and optionally the neural regeneration is detected inferentially by neurological examination.

A further aspect of the invention is the use of an EGFR inhibitor for the manufacture of a medicament to promote neural regeneration in a patient determined to have a lesion in a mature CNS neuron.

DETAILED DESCRIPTION OF SPECIFIC EMBODIMENTS OF THE INVENTION

The invention provides methods and compositions for promoting neural regeneration of a lesioned CNS neuron. As used herein, the singular forms "a," "an," and "the," refer to both the singular as well as plural, unless the context clearly indicates otherwise. For example, the term "a CNS neuron" includes both single and multiple neurons and can be considered equivalent to the phrase "at least one CNS neuron." In preferred embodiments, the neuron is a mammalian neuron, and in particular embodiments is a human neuron.

The lesioned neuron is subject to growth inhibition by endogenous myelin growth repulsion factors and may be in situ, i.e. located within the brain, brainstem, spinal cord, or optic nerve of a patient or animal model, or in vitro co-cultured with oligodendrocyte myelin or with isolated myelin growth repulsion factors such as myelin-associated glycoprotein (MAG), Nogo-A, and oligodendrocyte myelin glycoprotein (OMgp). The lesion may present at any part of the neuron. In particular embodiments a neurite (i.e. axon and/or dendrite) is lesioned, and the EGFR inhibitor treatment promotes neurite outgrowth. In one aspect, the invention provides a method of promoting neural regeneration in a patient determined to have a lesion in a mature (i.e. terminally-differentiated, non-embryonic) CNS neuron, preferably a post-gestational, juvenile, pediatric or adult CNS neuron, the method comprising the step of contacting the neuron with an EGFR inhibitor sufficient to promote regeneration of the neuron. The patient is a mammal such as a companion animal (dog, cat, etc.), livestock, animal model for neurodegeneration or CNS injury (e.g. rat, mouse, primate, etc), etc. In particular embodiments the patient is human.

The lesion can result from traumatic injury, stroke, pressure build-up, chronic neurodegeneration, etc. In a particular embodiment, the lesion results from acute or traumatic injury such as caused by contusion, laceration, acute spinal cord injury, etc. In this embodiment, the contacting step is preferably initiated within 96 hours of formation of the lesion, and more preferably within 72, 48, 24, or 12 hours. The EGFR inhibitor can be administered to the injured neuron in combination with, or prior or subsequent to, other treatment regimes such as the use of anti-inflammatory agents. In a specific embodiment, the lesion results from acute spinal cord injury and the method additionally comprises contacting the neuron with methylprednisolone sufficient to reduce inflammation of the spinal cord. In another embodiment, the lesion results from neurodegeneration which, for example, can be caused by neurotoxicity or a neurological disease or disorder such as Huntington's disease, Parkinson's disease, Alzheimer's disease, multiple system atrophy (MSA), glaucoma, etc.

The EGFR inhibitor can be any inhibitor that specifically suppresses EGFR function, including antisense and RNAi oligonucleotide inhibitors, peptide nucleic acids, peptide antagonists, monoclonal antibodies (MAB), small molecule inhibitors (SMI), etc. In addition, various molecules known to interfere with EGFR signaling such as EGFR truncations, Gene 33 polypeptide (also called RALT and MIG6), and kekkon can be targeted, introduced or expressed in target cells. For example, a wide variety of technologies are available for protein transfection, including the use of cationic liposomes, calcium phosphate coprecipitation, electroporation, microinjection, viral vectors, and a large number of commercially-available, proprietary lipid, polyamine and amphoteric protein reagents, including "ProJect", "TransIT", "Profect-1", "Chariot" and ProteoJuice". In a particular embodiment, the EGFR inhibitor is a small molecule or monoclonal antibody that specifically suppresses the kinase function of EGFR. Table I lists several small molecule and antibody EGFR inhibitors that are FDA-approved or are in clinical trials.

TABLE I

| Drug | Type | Company | Regulatory Status |
|---|---|---|---|
| Cetuximab | MAB | Imclone | Approved |
| Erlotinib | SMI | OSI-Pharmaceuticals | Approved |
| Gefitinib | SMI | AstraZeneca | Approved |
| Panitumumab | MAB | Abgenix | Phase II |
| TheraCIM | MAB | YM Biosciences | Phase II |
| EMD 72000 | MAB | Merck | Phase I |
| MDX447 | MAB | Medarex/Merck | Phase I |
| GW572016 | SMI | GlaxoSmithKline | Phase II |
| PKI166 | SMI | Novartis | Phase II |
| CI-1033 | SMI | Pfizer | Phase II |
| EKB-569 | SMI | Wyeth | Phase I |
| GW2016 | SMI | GlaxoSmithKline | Phase I |

The EGFR inhibitor can be contacted with the neuron using any suitable drug delivery method. For in vitro methods, the inhibitor is added to the culture medium, usually at nanomolar or micromolar concentrations (see Examples 1 and 3). For in situ applications, the EGFR inhibitor can be administered orally, by intravenous (i.v.) bolus, by i.v. infusion, intracranially, intraperitoneally, intraventricularly, by epidural, etc. Suitable protocols for administration of the EGFR inhibitor to a patient can be readily derived from the extensive animal studies and clinical trials that have been conducted on EGFR inhibitors for the treatment of cancer. In certain embodiments, the EGFR inhibitor is administered orally or intravenously. Several orally- and intravenously-administered EGFR inhibitors have shown to be well-tolerated and efficacious in glioma and other brain tumors, demonstrating that EGFR inhibitors delivered by these routes have a therapeutic effect on cells of the CNS. Small molecule EGFR inhibitors are typically administered orally at about 50-500 mg/day, and monoclonal antibodies are typically administered weekly by infusion at about 1-5 mg/kg body weight. In other embodiments, the EGFR inhibitor is contained within an implantable device specifically adapted for delivery to a CNS neuron. The devices include controlled release biodegradable matrices, fibers, pumps, stents, adsorbable gelatin (e.g. Gelfoam) or other devices loaded with pre-measured, discrete and contained amounts of an EGFR inhibitor sufficient to promote neuronal regeneration (see Example 5). In a particular embodiment, the device provides continuous contact of the neuron with the EGFR inhibitor at nanomolar or micromolar concentrations.

The subject methods may further comprise the step of detecting a resultant neural regeneration. For in vitro applications, neural regeneration can be detected by any routinely used method such as a neurite outgrowth assay (see Example 1). For in situ applications, neural regeneration can be detected using imaging methodologies such as MRI. More commonly, neural regeneration will be detected inferentially by neurological examination showing improvement in the patient's neural function. The detecting step may occur at any time point after initiation of EGFR inhibitor treatment, e.g. at least one day, one week, one month, three months, six months, etc. after initiation of treatment. In certain embodiments, the detecting step will comprise an initial neurological examination and a subsequent neurological examination conducted at least one day, week, or month after the initial exam. Improved neurological function at the subsequent exam compared to the initial exam indicates resultant neural regeneration. The specific detection and/or examination methods used will usually be based on the prevailing standard of medical care for the particular type of neural lesion being evaluated (i.e. trauma, neurodegeneration, etc.).

The invention also provides EGFR inhibitor-eluting or EGFR inhibitor-impregnated CNS-implantable solid or semi-solid devices. Examples of CNS implantable devices include polymeric microspheres (e.g. see Benny et al., Clin Cancer Res. (2005) 11:768-76) or wafers (e.g. see Tan et al., J Pharm Sci. (2003) 4:773-89), biosynthetic implants used in tissue regeneration after spinal cord injury (reviewed by Novikova et al., Curr Opin Neurol. (2003) 6:711-5), biodegradable matrices (see e.g. Dumens et al., Neuroscience (2004) 125:591-604), biodegradable fibers (see e.g. U.S. Pat. No. 6,596,296), osmotic pumps, stents, adsorbable gelatins (see e.g. Doudet et al., Exp Neurol. (2004) 189:361-8), etc. Preferred devices are particularly tailored, adapted, designed or designated for CNS implantation. The implantable device may contain one or more additional agents used to promote or facilitate neural regeneration. For example, in one embodiment, an implantable device used for treatment of acute spinal cord injury contains an EGFR inhibitor and methylprednisolone or other anti-inflammatory agent. In another embodiment, the implantable device contains an EGFR inhibitor and a nerve growth factor or hormone that promotes neural cell survival, growth, and/or differentiation, such as brain-derived neurotrophic factor (BDNF), ciliary neurotrophic factor (CNTF), nerve growth factor (NGF), etc.

EXAMPLE 1

EGFR Inhibitors Promote Neurite Outgrowth on a Myelin Substrate

We screened approximately 400 well-characterized small molecules in a neurite outgrowth assay of cerebellar granule cells (CGNs) on immobilized myelin substrate. Myelin was immobilized on 96-well plates using published methods (8). Individual compounds from a signaling molecule targeted drug library (TOCRIS) were diluted by 10-fold dilutions centered on their $IC_{50}$ values, in concentrations typically varying from low nanomolar to micromolar, and transferred to culture wells with $5 \times 10^4$ CGNs per well. Cells were grown overnight, fixed in paraformaldehyde, and stained with tubulin antibodies. Outgrowth was independently scored by two blind observers. Positively scored compounds were picked for further verifications. Each compound was evaluated at a $10^4$ dilution range centered on its $IC_{50}$ value to ensure effective concentrations for each drug tested. Several internal controls, including cAMP analogues, phosphodiesterase inhibitors, and a Rho-associated protein kinase inhibitor were identified in the screen, confirming previous findings and validating our approach. The majority of compounds tested did not have a noticeable effect on neurite outgrowth, and a small number of them were toxic. Surprisingly, several EGFR kinase inhibitors, including Tyrphostin B44(−), Tyrphostin A47 and Tyrphostin A46, showed the greatest ability to counter the effects of myelin inhibition, suggesting that EGFR kinase activity might play an important role in transducing myelin-dependent CNS outgrowth inhibition signals in neurons.

To confirm the involvement of EGFR kinase in myelin inhibition, we tested two well-characterized EGFR inhibitors with distinctive mechanisms of action, AG1478 and PD168393, and a non-receptor tyrosine kinase inhibitor, AG1288, in the outgrowth assay. P7-9 CGNs were plated on control and immobilized myelin substrate and grown in the presence of AG1288 (1 µM), AG1478 (10 nM) and PD168393 (10 nM) for 20 hr (8, 10). Cells were fixed in paraformaldehyde and stained with anti-tubulin antibody (Tuj1, Covance) to visualize and quantitate neurite length. The EGFR inhibitors AG1478 and PD168393, but not AG1288, effectively promoted neurite outgrowth from both CGNs and dorsal root ganglion (DRG) neurons when grown on substrates of whole myelin as well as individual myelin inhibitors, including Nogo-66 and MAG. Approximately 500 neurons were counted for each condition from at least 3 independent experiments. All AG1478 and PD168393 treatments on inhibitors were significant. In contrast, none of the treatments affected either the neurite outgrowth on a control poly-D-lysine (PDL) substrate or neuronal survival. Similarly, EGFR kinase inhibitors were able to block myelin neurite outgrowth inhibition in retinal explant cultures grown within a collagen matrix laden with myelin. P5-6 mouse retinas were dissected and cut into small explants on a tissue chopper. The resultant explants were cultured within a collagen matrix with and without myelin (10 µg/ml) in the presence or absence of PD168393 (10 nM) for 72 hrs. Explants were fixed and stained with anti-tubulin antibodies. PD168393 added to myelin cultures significantly promoted outgrowth of explants when compared to myelin alone (*Student's t test P<0.0001). These results indicated that EGFR inhibitors do not activate a general neurite outgrowth program, but rather interfere with signaling pathways required for the activity of myelin inhibitors.

EXAMPLE 2

CGNs Overexpressing Mutant EGFR and Grown on Myelin Exhibit Extensive Neurite Outgrowth To complement our results obtained from pharmacological manipulations, we made recombinant herpes simplex viruses (HSVs) that transduce expression of a mutant form of human EGFR in neurons (18, 19). The kinase deficient EGFR-K721A (kdEGFR) carries a point mutation in the kinase ATP-binding site (18, 19), and when over-expressed, can inhibit the activity of endogenous EGFR in a dominant-negative manner. Wild type (wtEGFR) and kinase-deficient EGFR (kdEGFR)HSV infected 2-2 cells were stimulated with 1 ng/ml EGF for 5 min and the lysates were immunoblotted with an antibody against pTyr1173 EGFR (Santa Cruz). Blots were stripped and reprobed with anti-EGFR antibodies. CGNs were infected with HSV viruses and plated on control and myelin substrates. The average neurite lengths were obtained. CGNs infected with mutant, but not wild type EGFR, exhibited extensive neurite outgrowth on myelin. These results indicated that EGFR kinase activity is required for myelin dependent neurite outgrowth inhibition.

EXAMPLE 3

Myelin Inhibitors Nogo-66 and OMgp Activate EGFR

Previous genetic studies have implicated EGFR in neuronal migration and axonal projection during development (20, 21); however, the expression and function of EGFR in the adult nervous system remains unclear. Using in situ hybridization, we found that EGFR was expressed in most parts of the mature nervous system, including the cerebral cortex, cerebellum, most DRG neurons, and retinal ganglion cells (RGCs). Furthermore, anti-EGFR antibodies immunostained both cell bodies and neurites of cultured DRG neurons and retinal explants.

To examine whether myelin inhibitors directly influence the activity of EGFR in myelin-responsive neurons, we treated serum-starved CGNs with recombinant soluble myelin inhibitors and assessed the EGFR receptor activity. By blotting neuronal lysates with antibodies directed against phosphorylated EGFR we found that both Nogo-66 and OMgp at 5 nM triggered EGFR phosphorylation as early as 1 min post-stimulation. This EGFR activation appeared to be specific for the myelin inhibitors as neither a control alkaline phosphatase (AP) protein nor the chemorepellant Semaphorin3A (Sema3A) induced detectable levels of EGFR phosphorylation. Additional evidence for EGFR activation was obtained by observing that Nogo-66-dependent ERK1/2 MAP kinase activation occurred in an EGFR kinase-dependent manner Previously, we developed a truncated form of NgR that has the ability to bind to ligands but not its signaling co-receptors (8-10, 12). When over-expressed, the truncated receptor can compete with endogenous NgR for coreceptor binding and thus block inhibitor-induced signaling pathways (8-10, 12). We found that expression of this truncated, but not full-length, NgR also efficiently blocked EGFR phosphorylation triggered by Nogo-66, suggesting that EGFR activation is NgRcomplex dependent. Next, we performed cell surface binding and co-immunoprecipitation experiments, but failed to detect either direct binding of EGFR to inhibitor ligands, or a physical association with NgR or p75. These results indicated that EGFR is not a receptor for myelin-derived inhibitors, nor is it likely part of the canonical NgR complex. It is known that in addition to activation by its cognate ligands, EGFR phosphorylation can also result from "trans-activation" by other signaling pathways (22, 23). For example, angiotensin II acts through the angiotensin AT1 receptor, to promote growth of cardiomyocytes via trans-activation of the EGFR and activation of MAP kinase (23). Failure to detect EGFR in the NgR receptor complex suggests a possible trans-activation of EGFR by signaling downstream of the active NgR receptor complex. In support of this, we found that the extent of EGFR phosphorylation triggered by optimal concentrations of myelin inhibitors was comparable to that resulting from low concentrations (1-2 ng/ml) of epidermal growth factor (EGF), reminiscent of what has been previously reported for EGFR trans-activation (24). Several molecules have been implicated in EGFR trans-activation, including $Ca^{2+}$, PKC, nonreceptor tyrosine kinases (Src and Pyk2), G-protein-coupled receptors, and metalloproteases that generate EGF-like ligands (22-25). We examined whether any of these mechanism(s) are involved in the NgR-dependent EGFR trans-activation by inhibiting specific signaling pathways pharmacologically. Only the calcium chelators EGTA and BAPTA-AM significantly decreased EGFR phosphorylation subsequent to Nogo-66 treatment. A PKC inhibitor Go6976, metalloprotease inhibitors TAPI and GM6001, a Src inhibitor PP2, and pertussis toxin, had no effect on Nogo-66 elicited EGFR phosphorylation. In further support of the idea of EGFR trans-activation, neither EGTA nor BAPTA-AM had any effect on direct EGFR activation by EGF. Thus, our results indicate EGFR transactivation is a critical downstream component of Ca2+ signaling in response to myelin inhibitors.

EXAMPLE 4

EGFR Inhibitors Neutralize the Neurite Outgrowth Inhibitory Activity of CSPGs

In addition to myelin inhibitors, chondroitin sulfate proteoglycans (CSPGs) in the glial scar represent a major hurdle for regenerating axons. Consistent with previous observations that CSPGs elevate intracellular $Ca^{2+}$ levels in responding neurons (26), we found that EGFR inhibitors could also neutralize the neurite outgrowth inhibitory activity of CSPGs. Retinal explants were grown in collagen gels with and without CPSGs (200 ng/ml, Chemicon) and PD168393 (100 nM) for three days, fixed and stained with anti-tubulin antibodies. PD168393 significantly increased neurite length of explants when compared to CSPGs alone. Furthermore, soluble CSPG added to serum-starved CGNs was able to elicit EGFR phosphorylation in a calcium-dependent manner. In contrast, neither growth cone collapse nor repulsive responses induced by Sema3A were affected by EGFR inhibitors. Since Sema3A has previously been suggested to act independently of intracellular $Ca^{2+}$ (27), these results further indicate that EGFR is a critical calcium-specific signaling molecule in axon guidance pathways.

EXAMPLE 5

EGFR Inhibition Promotes Regeneration of Lesioned Optic Nerve Fibers in Adult Mice The finding that inhibiting neuronal EGFR activity could efficiently block the inhibitory activity of both myelin inhibitors and CSPGs prompted us to examine whether EGFR inhibitors introduced at a CNS lesion site could promote axon regeneration in a model of optic nerve crushing (28). All animal experiments were done in accordance with protocols approved by the institutional animal care and use committee at Schepens Eye Research Institute. Adult mouse optic nerves were exposed behind the eyeball and crushed. Immediately after injury in adult mice, Gelfoam soaked in a solution containing the EGFR inhibitor PD168393 or 0.1% DMSO (control) was placed against the crush site of the nerve and replaced every three days for the first six days of the study. Animals were sacrificed two weeks post injury followed by transcardial perfusion with 4% paraformaldehyde. Optic nerves were cryosectioned at 10 µm and stained with an anti-GAP43 antibody (Chemicon) to detect regenerating axons (28). Little regeneration was detected in DMSO-treated control mice. However, suppression of EGFR kinase activity by injury site application of PD168393 resulted in substantial axonal regrowth with a 9-fold increase in the number of regenerating axons, measured 0.25 mm beyond the injury site, compared to control mice. To test the possibility that the observed axon regrowth of retinal ganglion neurons (RGCs) after PD168393 treatment was a consequence of improved cell survival, we stained retinal sections with the anti-tubulin Tuj1 antibody, which stains RGCs in the retina, and counted surviving RGCs. No detectable effect of PD168393 on RGC survival was found. Thus, blocking EGFR activity locally and within a short time window following injury is sufficient to promote significant regeneration of lesioned optic nerve fibers in adult mice.

EXAMPLE 6

Neuroprotective Effect of Gefitinib after Cortical Impact Injury in Rats

Using methodology adapted from Cherian et al. (J Pharmacol Exp Ther. (2003) 304:617-23), the effects of different doses and treatment schedules of gefitinib on a rat model of brain impact injury are tested. A total of 60 male Evans rats weighing 300 to 400 g are assigned to one of the following doses injected intraperitoneally (i.p.): none (saline control group), 1, 10, and 50 mg/kg/day gefitinib. The rats are further assigned to a treatment duration of 1, 3, 7, or 14 days, with 4 rats in each treatment group, and 3 rats in each control group (i.e. saline administered for 1, 3, 7, or 14 days).

The details of the methods to produce the impact injury have been previously described (Cherian et al., J. Neurotrauma (1996) 13:371-383). Briefly, the head of the rat is fixed in a stereotaxic frame by ear bars and incisor bar. A 10-mm diameter craniotomy is performed on the right side of the skull over the parietal cortex. An impactor tip having a diameter of 8 mm is centered in the craniotomy site perpendicular to the exposed surface of the brain at an angle of approximately 45 degrees to the vertical. The tip is lowered until it just touches the dural surface. The impactor rod is then retracted, and the tip advanced an additional 3 mm to produce a brain deformation of 3 mm during the impact. Gas pressure applied to the impactor is adjusted to 150 psi, giving an impact velocity of approximately 5 m/s and duration of approximately 150 to 160 ms.

Rats are fasted overnight and anesthetized with 3.5% isoflurane in 100% oxygen in a vented anesthesia chamber. Following endotracheal intubation with a 16-gauge Teflon catheter, the rats are mechanically ventilated with 2% isoflurane in 100% oxygen for the surgical preparation and for the impact injury. Intracranial pressure (ICP) is monitored by a 3F microsensor transducer (Codman & Schurtleff, Randolph, Mass.) inserted in the left frontal lobe, well away from the impact site. ICP is monitored during the impact injury as a measure of the severity of the injury. Rectal temperature is maintained at 36.5-37.5° C. by a heating pad, which is controlled by rectal thermistor. Brain temperature is kept constant at 37° C. with the help of a heating lamp directed at the head.

Each dose of gefitinib is dissolved in 1 ml of sterile 0.9% saline so that the volume delivered is the same for each group and only the dosage of gefitinib varies. The first dose is administered within 1 hour following impact injury. After removing all catheters and suturing the surgical wounds, the rats are allowed to awaken from anesthesia. For the first 3 days post injury, the rats are treated with butorphanol tartrate, 0.05 mg of i.m. every 12 h (twice a day), for analgesia and enrofloxacin 2.27%, 0.1 ml of IM qd, to reduce the risk of postoperative infections. Gefitinib is administered once daily for the assigned treatment duration.

The outcome measures are performed by investigators who are blinded to the treatment group. At 2 weeks after the impact, the animals are deeply anesthetized with a combination of ketamine/xylazine/acepromazine and perfused transcardially with 0.9% saline, followed by 10% phosphate buffered formaldehyde. The entire brain is removed and fixed in 4% formalin. The fixed brains are examined grossly for the presence of contusion, hematoma, and herniation. The brains are photographed, sectioned at 2-mm intervals, and then embedded in paraffin. Hematoxylin and eosin (H&E) stained 9-μm thick sections are prepared for histologic examination. Particular care is made to include the largest cross-sectional area of cortical injury on the cut surface of the embedded sections. The H&E-stained coronal sections are digitized using a Polaroid Sprint Scanner (Polaroid Corporation, Waltham, Mass.) equipped with a PathScan Enabler (Meyer Instruments, Houston, Tex.). The injury volume is measured by determining the cross-sectional area of injury in each H&E-stained coronal image and multiplying by the thickness of the tissue between the slices. This slab volume technique is implemented on the image processing program Optimas 5.2 (Optimas Corporation, Seattle, Wash.). Neurons in the middle 1-mm segments of the CA1 and CA3 regions of the hippocampus are counted at a magnification of 200×. Neurons are identified by nuclear and cytoplasmic morphology, and individual cells are counted whether normal or damaged. Neurons with cytoplasmic shrinkage, basophilia, or eosinophilia or with loss of nuclear detail are regarded as damaged. The regions measured are 1 mm long and 1 mm wide (0.5 mm on either side of the long axis of the segment). The total number of neurons and the number of neurons that appear normal are expressed as neurons per squared millimeter.

Gefitinib treatment regimes that demonstrate favorable neuroprotective effect are repeated in follow-up studies on rats divided into groups that receive a first dose of gefitinib at 1, 24, 48, 72, or 96 hours after brain impact injury, and the time window for the neuroprotective effect of gefitinib administration following traumatic brain injury is assessed.

EXAMPLE 7

Improved Neurological Outcome Following Cetuximab Treatment for Acute Spinal Cord Injury We adapted our protocol for this study from the Sygen® Multicenter Acute Spinal Cord Injury Study described by Geisler et al (Spine (2001) 26:587-598). It is a prospective, double-blind, randomized, stratified, multicenter trial, randomizing approximately 800 patients so as to have at least 720 completed and evaluable in each of three initial treatment groups: placebo, low-dose cetuximab, and high-dose cetuximab. The patients are stratified into six groups, according to three degrees of injury severity (American Spinal Injury Association grades A, B, and C+D) and two levels of anatomic injury (cervical and thoracic). The trial is sequential with preplanned interim analyses as each group of 720/4=180 patients reach their 26-week examination and become evaluable. Patients are required to have at least one lower extremity with a substantial motor deficit. Patients with spinal cord transection or penetration are excluded, as are patients with a significant cauda equina, brachial or lumbosacral plexus, or peripheral nerve injury. Gunshot injuries that do not penetrate the cord are allowed. Multiple trauma is allowed as long as it is not so severe as to prevent neurologic measurement evaluation or interpretation.

All patients are to receive the second National Acute Spinal Cord Injury Studies (NASCIS II) dose regimen of methylprednisolone (MPSS) starting within 8 hours after the spinal cord injury (SCI). To avoid any possible untoward interaction between MPSS and cetuximab the study medication is not started until after completion of MPSS administration.

The placebo group has a loading dose of placebo and then 56 days of placebo. The low-dose cetuximab group has a 300-mg loading dose administered intravenously (i.v.) followed by 100 mg/day i.v. for 56 days. The high dose cetuximab group has a 600-mg loading dose followed by 200 mg/day for 56 days.

The baseline neurologic assessment includes both the AIS and detailed American Spinal Injury Association (ASIA) motor and sensory examinations. Modified Benzel Classification and the ASIA motor and sensory examinations are performed at 4, 8, 16, 26, and 52 weeks after injury. The Modified Benzel Classification is used for post-baseline measurement because it rates walking ability and, in effect, subdivides the broad D category of the AIS. Because most patients have an unstable spinal fracture at baseline, it is not possible to assess walking ability at that time; hence the use of different baseline and follow-up scales. Marked recovery is defined as at least a two-grade equivalent improvement in the Modified Benzel Classification from the baseline AIS. The primary efficacy assessment is the proportion of patients with marked recovery at week 26. The secondary efficacy assessments include the time course of marked recovery and other established measures of spinal cord function (the ASIA motor and sensory scores, relative and absolute sensory levels of impairment, and assessments of bladder and bowel function).

EXAMPLE 8

Gefitinib Reduces Neurodegeneration in Mouse Model of Multiple System Atrophy

Multiple system atrophy (MSA) is a neurodegenerative disease that affects oligodendrocytes and CNS neurons. This study utilizes a recently developed mouse model of MSA (Yazawa et al, Neuron (2005) 45:847-859) to assess neurological outcome following gefitinib treatment. This MSA model is a transgenic mouse that overexpresses human α-synuclein, which accumulates in normal and degenerating axons and axon terminals in association with oligodendroglia and neuron loss and slowly progressive motor impairments. Mice are assigned to one of the following doses injected intraperitoneally (i.p.): none (saline control group), 1, 10, and 50 mg/kg/day gefitinib. Treatment is initiated with 1 month old mice. At 3, 6, 12, 18, and 24 months of age, motor testing is performed on gefitinib-treated and control mice using the rotarod treadmill test and wire hanging grip strength test. Mice are sacrificed at 12 and 24 months of age, brain sections are fixed, neural cell morphology is analyzed by transmission electron microscopy (EM), and the total number of neurons is counted.

Rotarod Treadmill Test: The accelerating rotarod treadmill (Ugo Basile, Italy) is used to analyze motor function of treated and control mice. Mice are given three trials with 45 min intertrial intervals on each of 2 consecutive days for 3 weeks. Each animal's endurance time (AET) is recorded, and the average of AETs is calculated.

Wire Hanging Grip Strength Test: Mice are placed with their forepaws on a horizontal wire and allowed to grasp the wire and remain suspended. Each mouse is given two trials with an intertrial interval of 2 hr. The total time the mice remain hanging on the wire is recorded as hanging times in seconds.

Transmission EM: Mice at 12 and 24 months of age (n=3 of each) are analyzed by transmission EM. The mice are deeply anesthetized and sacrificed by cardiac perfusion using 0.1 M cacodylate buffer (pH 7.4), followed by 4% paraformaldehyde and 2% glutaraldehyde. Cerebrum, pons, cerebellum, and lower thoracic spinal cord are fixed for 18 hr. Tissues are postfixed with 2% osmium tetraoxide for 1 hr and dehydrated and embedded in Epon. Ultra thin sections are cut and observed with a Joel 1010 transmission electron microscope (Peabody, Mass.).

Quantitative Analysis of Neurons and Oligodendrocytes: The total number of neurons in the L2 lumbar spinal cord as well as dopaminergic neurons in the substantia nigra is counted on sections from 12 and 24-month-old gefitinib-treated and control mice (each for n=3, 8 sections from each mouse). Cells are visualized by immunostaining with NeuN (Chemicon, Temecula, Calif.), an antibody that labels neuronal nuclei, and tyrosine hydroxylase (TH) (Pel-Freese, Brown Deer, Wis.). Quantitative analyses are conducted on photographs covering the entire area of interest with image analysis software, ImageProPlus (Media Cybernetics, Silver Spring, Md.). For oligodendrocyte analysis, cells are visualized by immunostaining with anti-CNP antibody. The total number of cells in the lumbar spinal cord sections from the treated and control mice (each for n=3, 8 sections) is manually counted.

EXAMPLE 9

Neuroprotective Effect of EGFR-specific shRNA

A rat model for transient global ischemia demonstrates the neuroprotective effect of EGFR-specific short hairpin RNA (shRNA) using methodology adapted from Ning et al., J. Neurosci. (2004) 24:4052-60.

An EGFR target sequence corresponding to nucleotides 2529-2557 of EGFR mRNA (accession no. X00588; see Zhang et al., Clin Cancer Res. (2004) 10:3667-77) is constructed into a pSUPER vector (see Brummelkamp et al, Science (2002) 296:550-553). A scrambled EGFR target sequence is used to construct control vectors. Plasmid transfections are done using LipofectAMINE 2000 (Invitrogen, Burlington, Ontario, Canada) as described previously (Wan et al., Nature (1997) 388:686-690).

Adult male Wistar rats weighing 200-300 gm are anesthetized with 2% halothane and placed in a David Kopf Instruments (Tujunga, Calif.) stereotaxic apparatus. EGFR-specific shRNA and vehicle are injected into the CA1 pyramidal cell layer of rats at the following coordinates: 3.5 mm posterior to bregma, 1.6 mm lateral from the midline, and at a depth of 3.0 mm from the skull surface. A volume of 1 μl of concentrated vector ($1 \times 10^6$ particles/μl) is injected into one side of the hippocampus at a rate of 0.05 μl/min.

Two days after plasmid injection the rats are anesthetized with 1.5% halothane, and the vertebral arteries are electrocauterized on day one. Twenty-four hours later, the animals are reanesthetized, and both common carotid arteries are clamped with aneurysm clips for 15 min. Animals are included for subsequent experiments only if they display an isoelectric EEG during the entire occlusion period, displayed a dilated pupil and a lack of corneal light reflex, and recover EEG activity within 30 min of reperfusion. Body temperature, as measured with a rectal thermometer, is maintained between 36.5 and 38° C. throughout the procedure with a heating lamp. Sham animals receive identical surgical exposure and handling without vessel occlusion.

At 48 hr after global ischemia, rats are perfused with 4% paraformaldehyde. Coronal sections (40 μm thick) through the dorsal hippocampus are cut on a sliding microtome and then processed for Fluoro-Jade B histochemical staining, which consistently reveals dying or degenerating neurons. Quantitative assessment is conducted by visually counting Fluoro-Jade B-stained neurons using a 20× objective lens. Average cell numbers are obtained by averaging counts over one consistent field at the middle point of the dorsal hippocampus where vectors and vehicle are injected and over three sections (80 μm apart) in each brain. The neuroprotective effect of EGFR-specific shRNA is demonstrated by a decrease in Fluoro-Jade B-stained neurons compared with controls.

The foregoing examples and detailed description are offered by way of illustration and not by way of limitation. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims

ENUMERATED REFERENCES

1. Schwab M E, Bartholdi D. Physiol Rev. 76, 319 (1996).
2. Goldberg J L, Klassen M P, Hua Y, Barres B A. Science 296, 1860 (2000).
3. Silver J, Miller J H. Nat Rev Neurosci. 5, 146 (2004).
4. Filbin M T. Nat Rev Neurosci. 4, 703 (2003).
5. McGee A W, Strittmatter S M. Trends Neurosci. 26, 193 (2003).
6. He Z, Koprivica V. Annu Rev Neurosci. 27, 341 (2004).
7. Fournier A E, GrandPre T, Strittmatter S M. Nature 409, 341 (2001).
8. Wang K C et al., Nature 417, 941 (2002)
9. Domeniconi M et al., Neuron 35, 283 (2002).
10. Wang K C, Kim J A, Sivasankaran R, Segal R, He Z. Nature 420, 74 (2002).
11. Mi et al., Nature Neurosci. 7, 221 (2004).
12. Park J B et al., Neuron 45, 345 (2005).
13. Zhao S et al., Neuron 45, 353 (2005).
14. Bandtlow et al., Science 259, 80 (1993).
15. Henley J R, Huang K H, Wang D, Poo M M. Neuron 44, 909 (2004).
16. Shim S et al., Nature Neurosci. 8, 730 (2005).
18. Felder S et al., Cell 61, 623 (1990).
19. Honegger et al., Proc Natl Acad Sci USA. 86, 925 (1989).
20. Garcia-Alonso L, Romani S, Jimenez F. Neuron 28, 741 (2000).
21. Wells A, Lillien L. Sci STKE. 253, pe47 (2004).
22. Lammers et al. J Biol Chem. 265, 16886 (1990).
23. Zwick et al. Trends Pharmacol Sci. 20, 408 (1999).
24. Andreev J et al. J Biol Chem. 276, 20130 (2001).

25. Rosen L B, Greenberg M E, Proc Natl Acad Sci USA 93, 1113 (1996).
26. Snow et al, Dev Biol. 166, 87 (1994)
27. Lehmann M et al., J. Neurosci. 19, 7537 (1999)
28. Fischer D, He Z, Benowitz L I. J. Neurosci. 18, 1646 (2004).

What is claimed is:

1. A method of promoting axonal regeneration in vitro by contacting mature CNS neurons that are cerebellar granule cells (CGNs), dorsal root ganglion cells (DRGs) or retinal ganglion cells (RGCs) following lesion injury, with a small molecule epidermal growth factor receptor (EGFR) inhibitor sufficient to promote axonal regeneration.

2. The method of claim 1 wherein the contacting is effected within 24 hours of formation of the injury.

3. The method of claim 1 further comprising the step of detecting a resultant regeneration.

4. The method of claim 1 wherein the EGFR inhibitor is selected from the group consisting of erlotinib, gefitinib, GW2016, GW572016, PKI166, CL-1033, EKB-569, and GW2016.

5. The method of claim 1 wherein the EGFR inhibitor is erlotinib.

6. A method of promoting axonal regeneration in vivo in a mouse by contacting mature CNS neurons that are retinal ganglion cells (RGCs) following optic nerve crush injury in said mouse, with a small molecule EGFR inhibitor sufficient to promote axonal regeneration.

7. The method of claim 6 wherein the contacting is effected within 24 hours of formation of the injury.

8. The method of claim 6 further comprising the step of detecting a resultant regeneration.

9. The method of claim 6 wherein the EGFR inhibitor is selected from the group consisting of erlotinib, gefitinib, GW2016, GW572016, PKI166, CL-1033, EKB-569, and GW2016.

10. The method of claim 6 wherein the EGFR inhibitor is erlotinib.

11. A method of promoting axonal regeneration in vivo in a human by contacting mature CNS neurons that are retinal ganglion cells (RGCs) following optic nerve crush injury in said mouse, with a small molecule EGFR inhibitor sufficient to promote axonal regeneration.

12. The method of claim 11 wherein the contacting is effected within 24 hours of formation of the injury.

13. The method of claim 11 further comprising the step of detecting a resultant regeneration.

14. The method of claim 11 wherein the EGFR inhibitor is selected from the group consisting of erlotinib, gefitinib, GW2016, GW572016, PKI166, CL-1033, EKB-569, and GW2016.

15. The method of claim 11 wherein the EGFR inhibitor is erlotinib.

16. The method of claim 11 wherein the contacting is effected within 24 hours of formation of the injury, the EGFR inhibitor is selected from the group consisting of erlotinib, gefitinib, GW2016, GW572016, PKI166, CL-1033, EKB-569, and GW2016, and the method further comprises the step of detecting a resultant regeneration.

* * * * *

UNITED STATES PATENT AND TRADEMARK OFFICE
CERTIFICATE OF CORRECTION

PATENT NO. : 7,449,442 B2  Page 1 of 1
APPLICATION NO. : 11/180070
DATED : November 11, 2008
INVENTOR(S) : Zhigang He and Vuk Koprivica It is certified that error appears in the above-identified patent and that said Letters Patent is hereby corrected as shown below:

Col. 14, line 12, "in said mouse" should be changed to -- in said human --.

Signed and Sealed this

Twenty-third Day of June, 2009

JOHN DOLL
*Acting Director of the United States Patent and Trademark Office*